US005602167A

United States Patent [19]
Carmosin et al.

[11] Patent Number: 5,602,167
[45] Date of Patent: Feb. 11, 1997

[54] 4-ARYLCYCLOHEPTA[C] PYRROLE ANALGESICS

[75] Inventors: Richard J. Carmosin, Quakertown; John R. Carson, Norristown; Philip M. Pitis, North Wales, all of Pa.

[73] Assignee: Ortho Pharmaceutical Corporation, Raritan, N.J.

[21] Appl. No.: 443,141

[22] Filed: May 17, 1995

[51] Int. Cl.$^6$ ...................... C07D 209/02; A61K 31/395
[52] U.S. Cl. ............................................. 514/412; 548/452
[58] Field of Search ............................. 548/452; 514/412

*Primary Examiner*—David B. Springer

[57] ABSTRACT

The 4-arylcyclopenta[c]pyrroles of the following formula are effective analgesics:

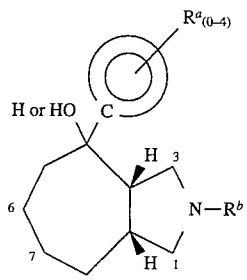

including stereoisomers and pharmaceutically acceptable salts thereof,
wherein

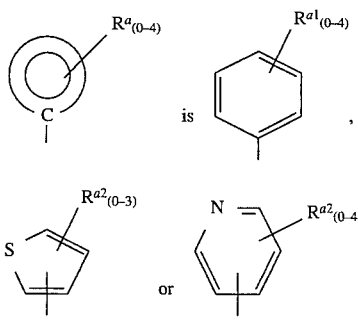

with the proviso that where there is a 4-position hydroxy then such is trans to the 3a and 6a hydrogens.

12 Claims, No Drawings

4-ARYLCYCLOHEPTA[C] PYRROLE ANALGESICS

The present invention relates to analgesics. More particularly, the present invention relates to 4-arylcyclohepta[c]pyrroles having analgesic activity.

BACKGROUND OF THE INVENTION

Analgesics used today in clinical practice suffer either from limited efficacy, limiting side effects or both. The non-steroidal antiinflammatory agents such as aspirin and ibuprofen fail to treat severe pain and cause gastrointestinal side effects. The opiates (morphine, codeine or meperidine) can treat more severe pain, but are subject to addiction liability and cause constipation and respiratory depression.

French Patent 8915407, to Rorer-Rhone Poulenc, discloses the compound:

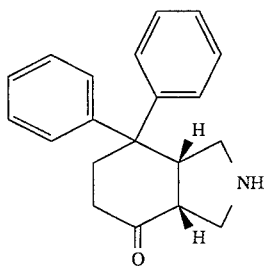

No biological utility is taught.

Eur. Pat. No. 430 771, to Rhone Poulenc, discloses the compound:

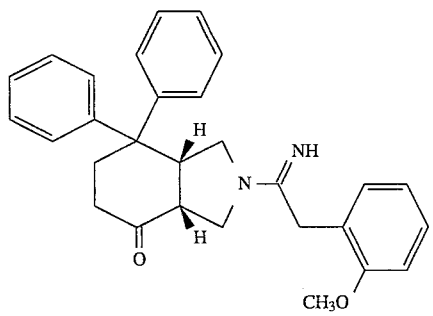

The biological utility is disclosed as a Substance P antagonist.

Ciba-Giegy has publicly disclosed the compound:

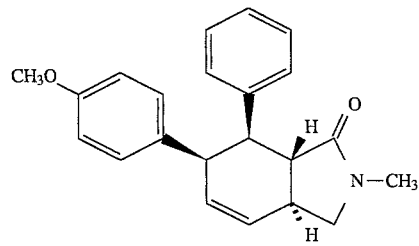

However, no biological activity was taught for this compound and its suitability for use as an analgesic is unknown.

U.S. Pat. No. 5,216,018, to Ciganek discloses isoindoles of the formula:

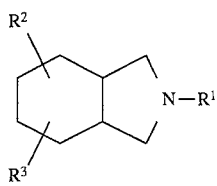

wherein $R^2$ and $R^3$ are disclosed among many other substituents to be independently phenyl. These compounds are disclosed as useful to treat physiological or drug induced psychosis and as antidyskinetic agents.

SUMMARY OF THE INVENTION

The present invention provides novel 4-arylcyclohepta[c]pyrroles having analgesic activity of the formula:

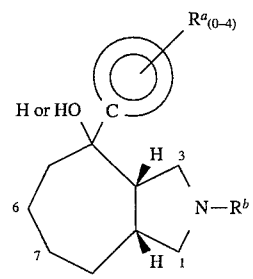

including the purified stereoisomers and pharmaceutically acceptable salts thereof,
wherein

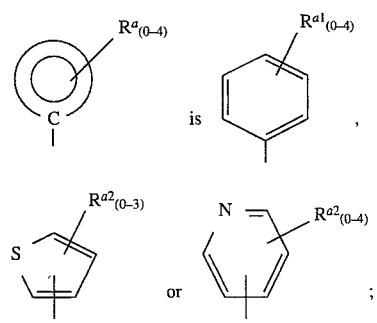

$R^{a1}$ is selected from the group consisting of halogen, $C_{1-4}$alkyl, substituted $C_{1-4}$ alkyl (wherein the substituent is $C_{1-4}$alkoxy, hydroxy or perhalo), $C_{1-4}$alkoxy, substituted $C_{1-4}$alkoxy (wherein the substituent is perfluoro), di($C_{1-4}$alkyl)amino, $C_{1-4}$alkylsulfonyl and phenyl;

$R^{a2}$ is selected from the group consisting of halogen or $C_{1-4}$alkyl; and $R^b$ is selected from the group consisting of hydrogen, $C_{1-4}$alkyl, $C_{1-4}$ alkenyl, $C_{1-6}$cycloalkylmethyl and $C_{1-6}$cycloalkyl;

with the proviso that where there is a 4-position hydroxy then such is trans to the 3a and 6a hydrogens.

DETAILED DESCRIPTION OF THE INVENTION

The compounds of Formula (I) can be divided into two basic structures:

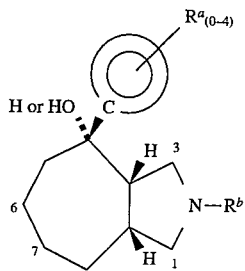

3aβ, 4β, 8aβ and
3aα, 4α, 8aα

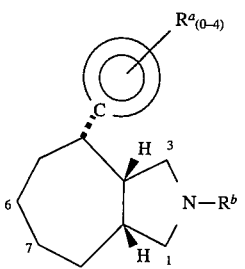

3aβ, 4α, 8aβ and
3aα, 4β, 8aα where $R^a$ and $R^b$ are as defined above. Unless specifically indicated otherwise, the structures herein represent the depicted stereoisomer as a racemic mixture.

Flow Sheets A and B illustrate the production of core 4-arylcyclohepta[c]pyrrole. In the Flow Sheets, the case in which the aryl is phenyl is exemplified. Each of the compounds represented by Formula I has three stereocenters and, in consequence, $2^3$ or 8 stereoisomers which include 4 diastereomers.

A: Synthesis of 4-hydroxy $1^a$

The 4-hydroxy $1^a$ of Flow Scheme A is obtained from commonly available starting materials which include cycloheptene-1-one, N-butoxyethyl-N-$R^b$-N-trimethylsilylmethylamine and phenyllithium. Of course, the equivalent lithiated pyridine or thiophene rather than phenyllithium would be employed in Flow Sheet A to obtain those alternate aryl moieties at the 4-position of the desired cyclohepta[c]pyrrole. The description herein using the phenyllithium is for exemplification only. In a first step, cycloheptene-1-one A1 is reacted with an azomethine ylide which results from the treatment of N-$C_{1-4}$alkoxymethyl-N-$R^b$-N-trimethylsilylmethylamine A2 with TFA in a literature cycloaddition of an azomethine ylide to an activated double bond to produce 2-$R^b$-3aα, 8aα-octahydrocyclohepta[c]pyrrol-4(1H) one A3. This cycloaddition may be carried out in a halocarbon solvent at reflux by simply adding the two reactants and subsequently adding trifluoroacetic acid (TFA). The reaction was found to be sensitive to the manner and amount of trifluoroacetic acid addition. Herein, a 1% solution of TFA was added to the reflux dropwise until the cycloaddition was complete. Subsequently, the ketone A3 is reacted with the aryllithium by mixing the reactants in a solvent, such as, diethyl ether, THF or hexane and allowing the mixture to stir for 1–6 hours at from –78° C. to room temperature to produce 2-$R^b$-4α-phenyl-3aα, 8aα-decahydrocyclohepta[c]pyrrol-4βol $1^a$.

FLOW SCHEME A

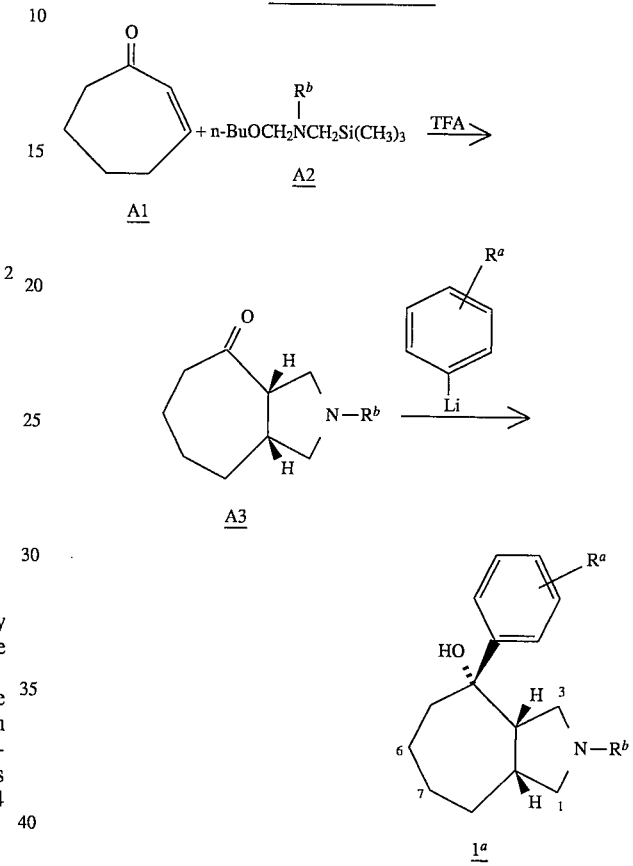

B: Synthesis of 2

Compounds $1^b$ and 2 of Flow Scheme B are obtained from 4-hydroxy $1^a$. Of course, the equivalent 4-hydroxy $1^a$ with pyridine or thiophene rather than phenyl would be employed in Flow Sheet B as the starting material to obtain these alternate aryl moieties at the 4-position of the desired cyclohepta[c]pyrrole. The description herein using the phenyl bearing cyclohepta[c]pyrrole is for exemplification only. To obtain a mixture of $1^b$ and 2, 4-hydroxy $1^a$ is subjected to hydrogenolysis over palladium in the presence of an acid. Alternatively, the transformation may be carried out by dehydration of $1^a$ to the 4,5-olefin caused by treatment with a protic acid followed followed by hydrogenation over Raney nickel or over a noble metal, such as, palladium, platinum, rhodium or nickel, with or without heat and at pressures from atmospheric to 100 psi. The acid in either case may be selected from acetic acid, perchloric acid, sulfuric acid or p-toluenesulfonic acid.

FLOW SCHEME B

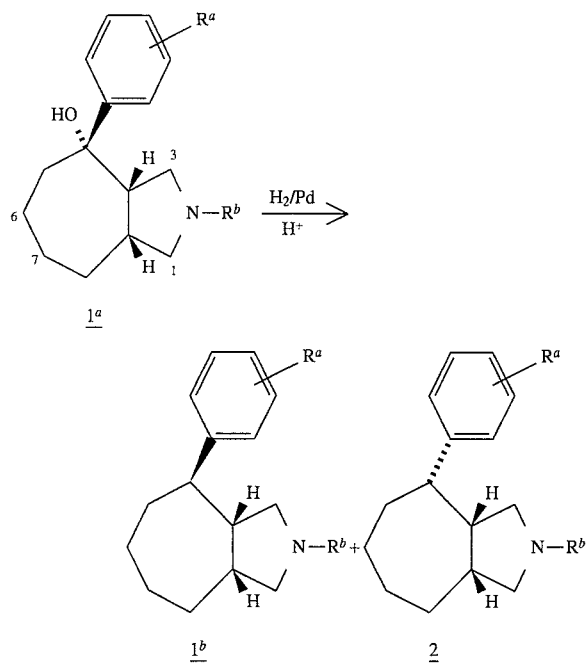

As seen, Flow Sheets A and B show the production of diastereomers. Each diastereomer may be separated into individual enantiomers using chiral HPLC techniques. Such techniques are well known in the art. Suitable columns on which chiral HPLC separations may be carried out are available on the market and include CYCLOBOND 1-2000, manufactured by ASTEC COMPANY of Whippany, N.J. Alternatively, classical resolution employing a chiral acid may be used to produce individual enantiomers. Suitable chiral acids include D or L tartaric acids and D or L bromocamphorsulfonic acids.

The manufacture of starting materials described above is well known. Starting material A2 may be obtained by heating methylamine and chloromethyltrimethylsilane to produce N-methyl-N-trimethylsilylmethylamine and adding this material dropwise to a solution of aqueous formaldehyde followed by the addition of butanol and potassium carbonate. Analogous A2 such as N-benzyl and N-cyclohexyl may be similarly produced. Starting material A 1 may be purchased or produced by well known methods. The phenyllithium of Flow Scheme A may be prepared by the reaction of lithium metal with bromo or chlorobenzene. The analogous bromo or chlorothiophene or pyridine will produce the analogous thienyllithium-or pyridyllithium.

Preferred $R^{a1}$ are selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, dimethylamino, diethylamino, methylethylamino, methylsulfonyl, ethylsulfonyl, n-propylsulfonyl and phenyl;

Preferred $R^{a2}$ are selected from the group consisting of bromine, chlorine, fluorine, methyl, ethyl, n-propyl, i-propyl or t-butyl.

Preferred $R^b$ are selected from the group consisting of hydrogen, methyl, ethyl, n-propyl, i-propyl, t-butyl, allyl, cyclopropylmethyl, cyclopropyl and cyclohexyl.

Preferred compounds of Formula (I) above have base structures selected from the group consisting of:

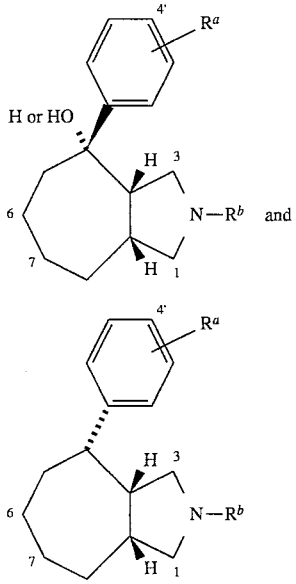

wherein $R^a$ and $R^b$ are simultaneously selected from the group consisting of the groups:

| $R^a$ | $R^b$ |
| --- | --- |
| 4'-F | Me |
| 3'-methoxy | Me |
| 3'-CF$_3$ | Me |
| 3'-methoxy | cyclopropyl-Me |
| 2',3'-dimethoxy | Me |
| 3',4'-dichloro | Me |
| — | Me |
| 4'-CF$_3$ | Me |
| 3'-CF$_3$ | n-butyl |
| 4'-Cl | Me |
| 2'-Cl | Me |
| 2',5'-dichloro | Me |
| 4'-F | Me |
| 4'-methoxy | Me |
| 3',4'-dimethoxy | Me |
| 4'-i-propyl | Me |
| 4'-Br | Me |
| 4'-SO$_2$Me | Me and |
| 3'-methoxy | cyclopropyl | including the purified enantiomers thereof.

The most preferred compounds of Formula I are:

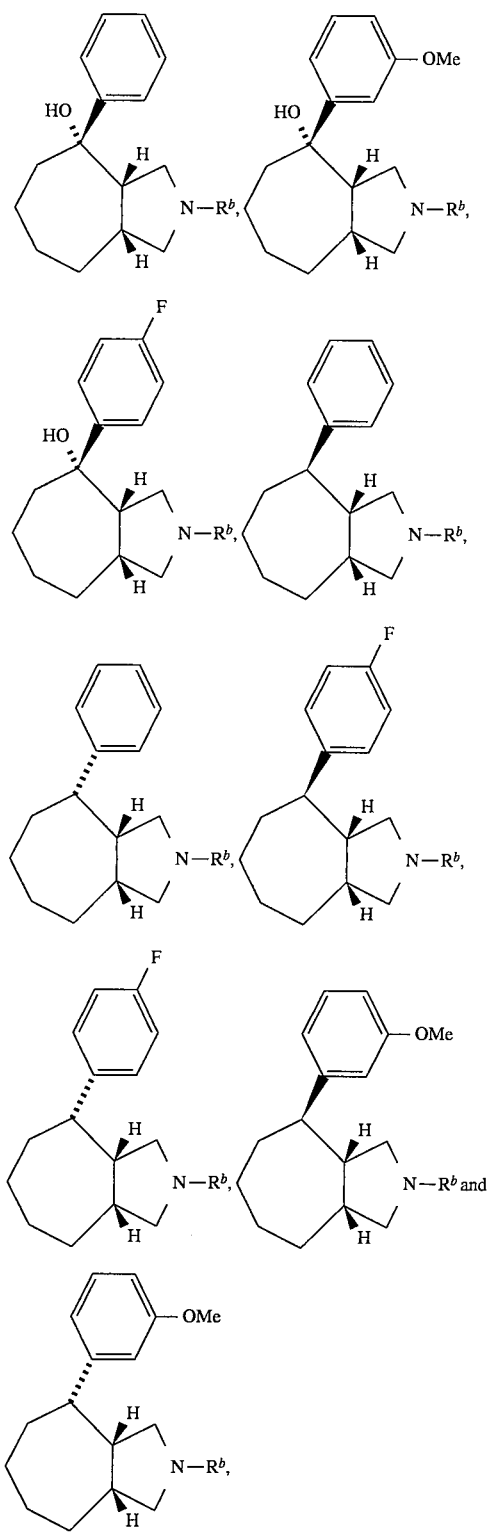

including the racemic mixtures and purified enantiomers of each.

The activity of compounds of the invention as analgesics may be demonstrated by the mouse acetylcholine-bromide induced constriction assay as described below:

Mouse Acetylcholine Bromide-Induced Abdominal Constriction Assay

The mouse acetylcholine-induced abdominal constiction assay, as described by Collier et al. in Brit. *J. Pharmacol. Chem. Ther.*, 32:295–310, 1968, with minor modifications was used to assess analgesic potency of the compounds of formula (I). The test drugs or appropriate vehicle were administered orally (p.o.) and 30 minutes later the animal received an intraperitoneal (i.p.)injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the No. of control animals response and the No. of drug-treated animals response times 100 divided by the No. of control animals responding.

TABLE I

Mouse Acetylcholine-Bromide Induced Abdominal Constriction Assay

| Compound Number | % Inhibition at 30 mg/kg (route) |
| --- | --- |
| Cp-1 | 93 (po) |
| Cp-2 | 80 (po) |
| Cp-3 | 100 (po) |
| Cp-4 | 80 (po) |
| Cp-5 | 100 (po) |
| Cp-6 | 93 (po) |
| Cp-7 | 100 (po) |
| Cp-8 | 100 (sc) |
| Cp-9 | 90 (sc) |

Based on the above results, invention compounds of formula (I) may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 or 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carders are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the nitrogen of the core ring and/or possibly a nitrogen of a substituent is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

EXAMPLES

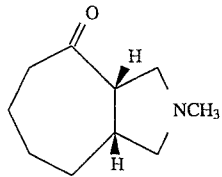

Procedure A

2-Methyl-3aα,8aα-octahydrocyclohepta-[c]pyrrol-4(1 H)-One

A solution of 22.5 g (0.11 moles) N-butoxyethyl-N-methyl-N-trimethylsilylmethylamine, 45 mL of dry $CH_2Cl_2$, 9.45 mL (0.085 moles) of 2-cycloheptene-1-one and 45 drops of 1% TFA reflux for one hour. Another 120 drops of 1% TFA in $CH_2Cl_2$ was added in portions at 20 min intervals. It was heated under reflux for a further 30 min. Solid $K_2CO_3$ was added and the reaction was stirred for 20 min. Water was added, the organics were separated, washed with water, brine and dried ($K_2CO_3$). The solvent was evaporated in vacuo to give 16 g of an oil.

An analytical sample was obtained by flash chromatography (silica gel, 90:10:1 $CH_2Cl_2$:MeOH:$NH_4OH$). The resulting product was converted to the oxalate salt in 2-PrOH. mp 129°–131° C.; mass spectrum (Cl—$CH_4$) m/z= 168 (M+1); NMR 300 MHz($Me_2SO$-$d_6$)δ3.65–3.8 (m, 2H); 2.9–3.5 (m, 2H); 2.75 (s, 3H); 2.7–2.5 (m, 2H); 2.4–2.2 (m, 2H); 1.9 (m, 2H); 1.75(m,2H); 1.55–1.3(m, 2H). Anal calcd for $C_{10}H_{17}NO$-$C_2H_2O_4$ 0.8 $H_2O$:C, 54.49; H, 7.55; N, 5.30 Found: C, 54.44; H, 7.39; N, 5.37.

Example 1

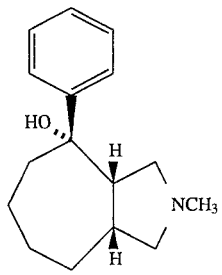

2-Methyl-4α-Phenyl-3aα, 8aα-Decahydrocyclohepta-[c]pyrrol-4β-ol

A solution of 8.4 mL of bromobenzene in 75 mL of THF was added dropwise to a solution of 32.4 mL (0,081 moles) 2.5M n-BuLi in hexanes under argon at −60°. After stirring for 3h, a solution of 5.2 g (0.031 moles) 2-methyl-3aα, 7aα-octahydrocyclohepta[c]pyrrol-4(1H)-one in 50 mL of THF was added dropwise and the reaction was stirred for 1.25 h at −78° C. The reaction was poured into water, the organics were washed with water, brine, and dried ($K_2CO_3$). The solvent was removed in vacuo to give a tan solid. Recrystallization from acetonitrile gave 3.57 g of 2-methyl-4α-phenyl-3aα, 8aα-decahydrocyclohepta[c]pyrrol-4β-ol. mp 110°–112° C. mass spectrum (Cl—$CH_4$) m/z=246 (M+1). 300 MHz ($CDCl_3$) β7.4–7.1 (Ar, 5H); 4.15 (bs, 1H); 2.7 (m, 1H); 2.6–2.5 (m, 2H); 2.35 (m, 1H); 2.2 (dd, 1H); 2.1 (s 3H); 2.05 (m, 2H); 1.9–1.8 (m, 5H); 1.7 (m, 2H). Anal calcd. for $C_{16}H_{23}NO$:C, 78.32; H, 9.45; N, 5.71. Found: C, 78.15; H, 9.42; N, 5.43.

Example 2

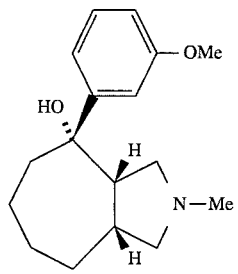

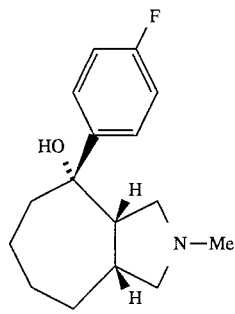

Using the procedure of Example 1 and employing the appropriate arylbromide in place of bromobenzene there was obtained the following products:

4α-(3-Methoxyphenyl)-2-methyl-3aα, 8aα-decahydrocyclohepta[c]pyrrol-4β-ol. mp. 95°–97° C. mass spectrum (Cl—$CH_4$) m/z=276 (M+1). 300 MHz NMR ($CDCl_3$)δ7.5 (Ar, 1H); 7.1 (Ar, 1H); 6.95 (Ar, 1H); 6.75 (Ar, 1H); 4.3 (bs, 1H); 3.8 (s, 3H); 2.5–2.7 (m, 2H); 2.5–2.3 (m, 2H); 2.25 (dd, 1H); 2.15 (s, 3H); 2.0 (m, 1H); 1.95–1.6 (m, 8H). Anal calcd for C₁₇H₂₅NO₂–0.16 CH₃CN:C, 73.78; H, 9.11; N, 5.76. Found: C, 73.78; H, 9.14; N, 5.66.

4aα-( 4-Fluorophenyl)-2-methyl-3aα, 8aα-decahydro-cycloheptα[c]pyrrol-4β-ol. mp 103°–105° C. mass spectrum (Cl—CH₄) m/z=264 (M+1). 300 MHz NMR (CDCl₃) δ7.4 (Ar, 2H); 7.0–7.1 (Ar, 2H); 4.8 (bs, 1H); 2.8 (t, 1H); 2.6–2.5 (m,1H); 2.4–2.25 (m, 1H); 2.05 (s, 3H); 2.0 –1.9 (m, 3H); 1.8–1.7 (m, 5H); 1.6–1.5 (s, 2H); 1.35–1.25 (m, 1H). Anal calcd for C₁₆H₂₂FNO:C, 72.97; H, 8.26; N, 5.32. Found: C, 72.66; H, 8.26; N, 5.18.

Example 3

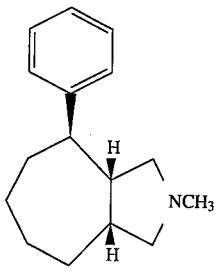

Cp-4

2-Methyl-4α-phenyl-3aα,8aα-decahydrocyclohepta-[c]pyrrole

A solution of 3.4 g ( 0.013 moles) 2-methyl-4 α-phenyl-3aα, 8aα-decahydrocyclohepta[c]pyrrol-4 δ-ol, 80 mL of acetic acid, and 7.4 mL of 70% perchloric acid were placed in a Parr bottle over 1.5 g of 10% palladium on carbon and hydrogenated under 55 psi hydrogen overnight. The catalysts was filtered off and the filtrate was concentrated in vacuo. The residue was partitioned between diethyl ether and 3N NaOH, the organics were washed with water, brine and dried (K₂CO₃). The solvent was evaporated in vacuo. The two resulting diastereomers were separated by Waters prep 500 HPLC on silica columns with 95:5:0.5 CH₂Cl₂:MeOH:NH₄OH as elutant. The first diastereomer to elute was 2-methyl-4α-phenyl-3aα, 8a α-decahydro cyclohepta[c]pyrrole. It was partitioned between diethyl ether and 3N NaOH, washed with brine and dried (K₂CO₃). The solvent was evaporated in vacuo. The residue was converted to oxalate salt, yield, 0.78 g: mp 143°–145° C. mass spectrum (Cl—CH₄) m/z=320 (M+1). 300 MHz NMR (Me₂SO-d₆) δ7.3–7.2 (Ar, 5H); 3.6 (bm, 1H); 2.75 (m, 4H); 2.7 (s, 3H); 2.6–2.5 (m, 1H); 1.9–1.6 (m, 7H); 1.5–1.2 (m, 2H). Anal calcd for C₁₆H₂₃N-C₂H₂O₄:C, 67.69; H, 7.89; N, 4.39. Found: C,67.44; H, 7.93; N, 4.26.

Example 4

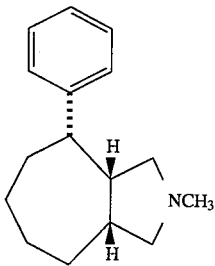

Cp-5

2-Methyl-4β-phenyl-3aα, 8aα-decahydrocyclohepta[c]pyrrole

Further elution of the chromatography column of Example 3 afforded the second diastereomer, 2-methyl-4β-phenyl-3aα, 8aα-decahydrocyclohepta[c]pyrrole. It was converted to its fumarate salt (0.95 g): mp 134°–135° C. mass spectrum (Cl—CH₄) m/z=230 (M+1). 300 MHz NMR (Me₂SO-d₆) δ7.3–7.1 (Ar, 5H); 6.5 (s, 2H); 3.1 (m, 2H); 2.9 (m, 1H); 2.65–2.55 (m, 3H); 2.55 (s, 3H); 2.1 (q, 1H); 1.8 (m, 1H); 1.7 (m, 4H), 1.6 (m, 2H ); 1.3 (m, 1H). Anal calcd for C₁₆H₂₃N-C₄H₄ O₄:C, 69.31; H, 7.95; N, 3.95. Found: C, 69.00; H, 7.93; N, 3.95.

Example 5

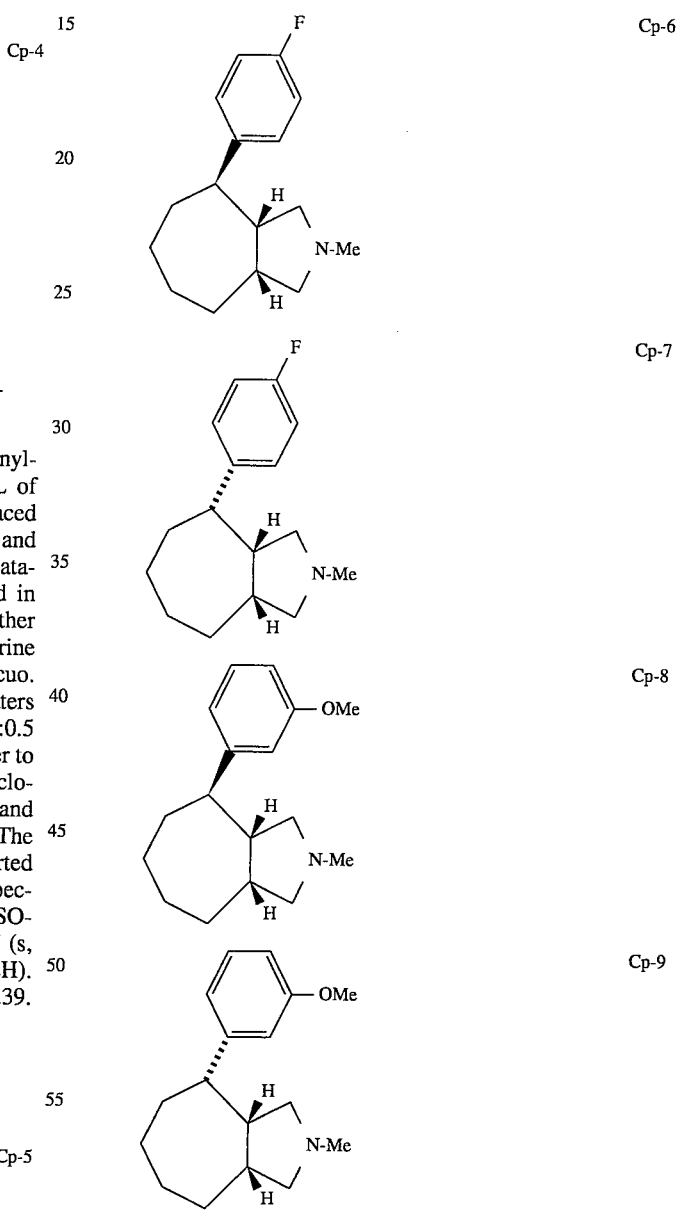

Using the procedures of Examples 3 and 4 and employing the appropriate 2-methyl-4α-aryl-3aα, 8aα-decahydrocyclohepta[c]pyrrol-4β-ol in place of 2-methyl-4≠obtained the following products:

4α-( 4-Fluorophenyl)-2-methyl-3aα, 8aα-decahydrocyclohepta[c]pyrrole oxalate. mp 151°–153° C. mass spectrum (Cl—CH₄) m/z=248 (M+1). 300 MHz NMR (Me₂SO-d₆) δ7.2 (Ar, 4H); 3.75 (bdd,2H), 3.6 (m, 1H);

3.1 (m, 1H); 3.0 (m, 1H); 2.7 (s, 3H); 2.7 —2.55 (m, 2H); 2.4 (m, 2H); 2.0 (m, 1H); 1.9–1.5 (m, 3H); 1.5–1.3 (m, 2H). Anal calcd for $C_{16}H_{22}FN\text{-}C_2H_2O_4$:C, 64.08; H, 7.17; N, 4.15; Found: C, 64.18; H, 6.83; N, 4.01.

4β-(4-Fluorophenyl)-2-methyl-3aα, 8aα-decahydrocyclohepta[c]pyrrole fumarate. mp 115°–117° C. mass spectrum (Cl—CH$_4$) m/z=248 (M+1). 300 MHz NMR (Me$_2$SO-d$_6$) δ7.25 (Ar, 2H); 7.1 (Ar, 2H); 6.5 (s, 2H); 3.3 (t, 1H); 2.7–2.5 (m, 2H); 2.5 (s, 3H); 2.5–2.4 (m, 2H); 2.15 (m, 2H); 1.9–1.2 (m,8 ). Anal calcd for $C_{16}H_{22}FN\text{-}C_4H_4O_4$:C,66.10; H, 7.21; N, 3.85. Found: C, 65.85; H, 7.17; N, 3.78.

4α-(3-methoxyphenyl)-2-methyl-3aα, 8aα-decahydrocyclohepta[c]pyrrole oxalate hydrate. mp 112°–115° C. mass spectrum (Cl—CH$_4$) m/z=260 (M+1 ). 300 MHz NMR (Me$_2$SO-d$_6$) δ7.25 (Ar, 1H); 6.8 (Ar, 3H); 3.7 (s, 3H); 2.9–2.7 (m, 3H); 2.7 (s, 3H); 2.6–2.55 (m, 4H); 1.9–1.6 (m, 6H); 1.5–1.3 (m, 2H). Anal calcd for $C_{17}H_{25}NO\text{-}C_2H_2O_4\cdot 0.2H_{20}$:C, 64.64; H, 7.82; N, 3.97; KF, 1.0. Found: C,64.29; H, 7.67; N, 3.86; KF, 0.65.

4β-(3-methoxyphenyl)-2-methyl-3aα, 8a α-decahydrocyclohepta[c]pyrrole oxalate hydrate. mp 146°–147° C. mass spectrum (Cl—CH$_4$) m/z=260 (M+1). 300 MHz NMR (Me$_2$SO-d$_6$), δ7.2 (Ar, 1H); 6.75 (Ar, 3H); 3.7 (s, 3H); 2.8 (m, 2H); 2.7–2.6 (m, 3H); 2.65 (s, 3H); 2.55–2.5 (m, 3H); 1.85–1.6 (m, 5H); 1.4 (m, 2H). Anal calcd for $C_{17}H_{25}NO\text{-}C_2H_2O_4\text{-}0.1H_2O$:C, 64.97; H, 7.81; N, 3.99; KF, 0.91. Found:C, 64.73; H, 7.71; N, 3.89; KF, 1.0.

What is claimed is:

1. A compound having analgesic activity of the general formula:

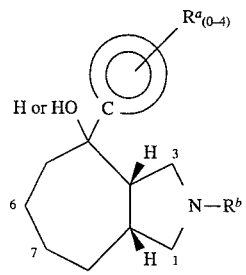

including the purified stereoisomers and pharmaceutically acceptable salts thereof, wherein

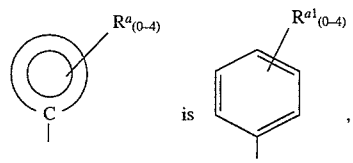

$R^{a1}$ is selected from the group consisting of halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), di($C_{1-4}$alkyl)amino, $C_{1-4}$alkylsulfonyl and phenyl;

$R^{a2}$ is selected from the group consisting of halogen or $C_{1-4}$alkyl; and $R^b$ is selected from the group consisting of hydrogen, $C_{1-4}$ alkyl, C1–4alkenyl, $C_{1-6}$cycloalkylmethyl and $C_{1-6}$cycloalkyl;

with the proviso that where there is a 4-position hydroxy then such is trans to the 3a and 6a hydrogens.

2. The compound of claim 1 of the general formula:

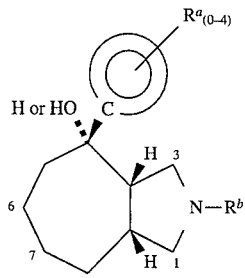

including the purified stereoisomers thereof.

3. The compound of claim 1 of the general formula:

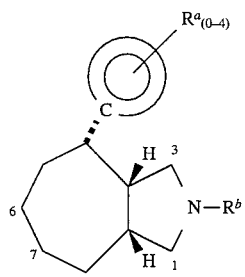

including the purified stereoisomers thereof.

4. The compound of claim 1 wherein:

$R^{a1}$ are selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, dimethylamino, diethylamino, methylethylamino, methylsulfonyl, ethylsulfonyl, n-propylsulfonyl and phenyl.

5. The compound of claim 1 wherein:

$R^{a2}$ is selected from the group consisting of bromine, chlorine, fluorine, methyl, ethyl, n-propyl, i-propyl and t-butyl.

6. The compound of claim 1 wherein:

$R^b$ is selected from the group consisting of hydrogen, methyl, ethyl, n-propyl, n-propyl, i-butyl, allyl, cyclopropylmethyl, cyclopropyl and cyclohexyl.

7. The compound of claim 1 wherein said pharmaceutically acceptable salt is a salt made with an acid selected from the group consisting of hydrochloric, hydrobromic, hydroiodic, perchloric, sulfuric, nitric, phosphoric, acetic, proprionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic and a salt made with sacchrine.

8. A compound having a structure selected from the group consisting of:

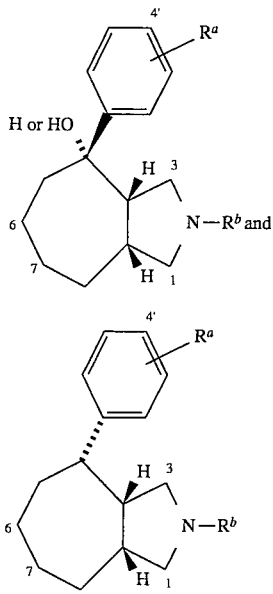

wherein $R^a$ and $R^b$ are simultaneously selected from the group consisting of the groups:

| $R^a$ | $R^b$ |
|---|---|
| 4'-F | Me |
| 3'-methoxy | Me |
| 3'-CF$_3$ | Me |
| 3'-methoxy | cyclopropyl-Me |
| 2',3'-dimethoxy | Me |
| 3',4'-dichloro | Me |
| — | Me |
| 4'-CF$_3$ | Me |
| 3'-CF$_3$ | n-butyl |
| 4'-Cl | Me |
| 2'-Cl | Me |
| 2',5'-dichloro | Me |
| 4'-F | Me |
| 4'-methoxy | Me |
| 3',4'-methoxy | Me |
| 3',4'-dimethoxy | Me |
| 4'-i-propyl | Me |
| 4'-Br | Me |
| 4'-SO$_2$Me | Me and |
| 3'-methoxy | cyclopropyl | including the purified enantiomers thereof.

9. The compound of claim 1 selected from the group consisting of:

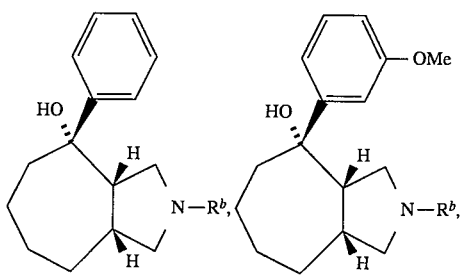

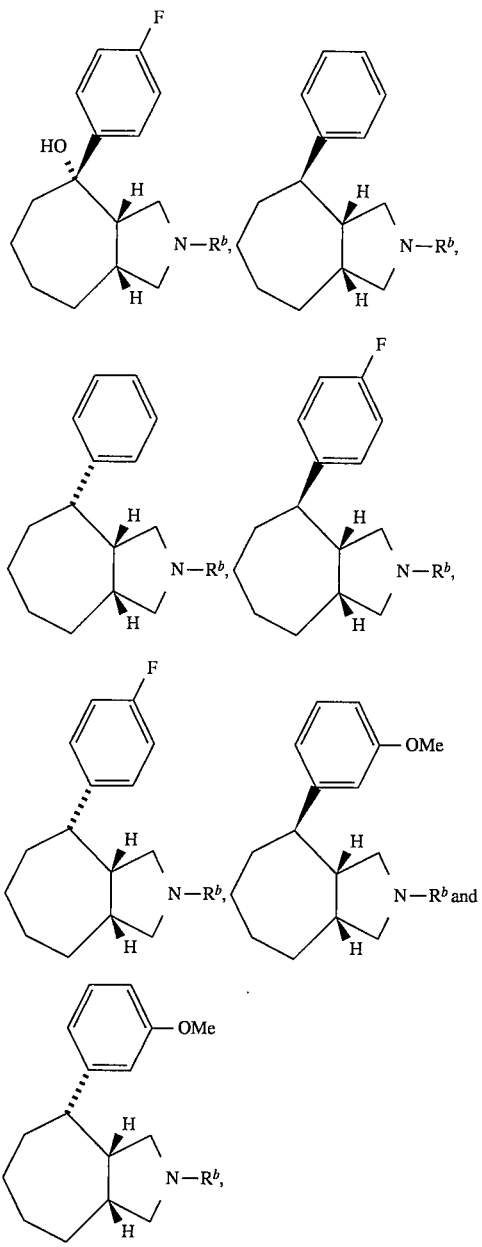

including the racemic mixtures and purified enantiomers of each.

10. A pharmaceutical composition effective as an analgesic in mammals comprising a phamaceutically acceptable carrier and an effective amount of the compound of claim 1.

11. A method for inducing an analgesic effect in mammals comprising the step of administering an effective amount of the compound of claim 1 in admixture with a pharmaceutically acceptable carrier.

12. A compound selected from the group consisting of:
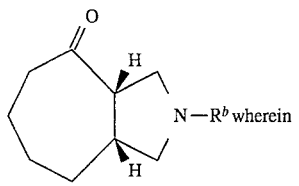
wherein
$R^b$ is selected from the group consisting of hydrogen, methyl, ethyl, n-propyl, i-propyl, t-butyl, allyl, cyclopropylmethyl, cyclopropyl and cyclohexyl.
* * * * *